United States Patent [19]
Casey

[11] Patent Number: 4,521,310
[45] Date of Patent: Jun. 4, 1985

[54] APPARATUS AND METHOD FOR THE TREATMENT OF ORGANIC WASTES

[76] Inventor: Thomas J. Casey, 22 Ardagh Ave., Blackrock, County Dublin, Ireland

[21] Appl. No.: 527,745

[22] Filed: Aug. 30, 1983

[30] Foreign Application Priority Data

Aug. 31, 1982 [IE] Ireland ................... 2115/82

[51] Int. Cl.³ .................................. C02F 3/28
[52] U.S. Cl. ..................... 210/603; 210/608; 210/613; 210/97; 210/137; 210/138; 210/180; 210/188; 210/195.1; 210/197
[58] Field of Search ............... 210/603, 605, 607, 608, 210/613, 97, 741, 748, 137, 138, 180, 188, 198.3, 197; 435/167

[56] References Cited

U.S. PATENT DOCUMENTS

| | | | |
|---|---|---|---|
| 1,690,682 | 11/1928 | Imhoff | 210/608 |
| 2,202,772 | 5/1940 | Durdin | 210/603 |
| 2,422,394 | 6/1947 | Carton | 210/608 |
| 3,338,826 | 8/1967 | Kramer | 210/613 |
| 3,887,459 | 6/1975 | McLaughlin | 210/748 |
| 4,211,647 | 7/1980 | Friedman | 210/603 |
| 4,293,421 | 10/1981 | Green | 210/603 |
| 4,302,329 | 11/1981 | Pfefferkorn | 210/180 |
| 4,429,043 | 1/1984 | Paton | 210/603 |

FOREIGN PATENT DOCUMENTS

| | | | |
|---|---|---|---|
| 2919532 | 11/1980 | Fed. Rep. of Germany | 210/603 |
| 158700 | 2/1983 | German Democratic Rep. | 210/603 |
| 58-74192 | 5/1983 | Japan | 210/603 |

Primary Examiner—Ernest G. Therkorn
Attorney, Agent, or Firm—Birch, Stewart, Kolasch & Birch

[57] ABSTRACT

Apparatus for the anaerobic conversion of organic waste to biogas using a microbial biomass comprises a closed reactor (1) adapted to receive the organic waste, the reactor having a first chamber (4) and a second chamber (3) in liquid communication, a gas blower (13) for conveying biogas which accumulates in the second chamber (3) to the first chamber (4) with a corresponding displacement of liquid material from the first chamber (4) to the second chamber (3), and a quick-release valve (14) for rapidly equalizing gas pressure in the chambers with a concomitant rapid reverse displacement of liquid material at predetermined intervals, resulting in an oscillating flow of liquid material in the reactor and an intimate mixing of the organic waste and the biomass, and a gas outlet (17) for releasing biogas from either of the chambers.

12 Claims, 1 Drawing Figure

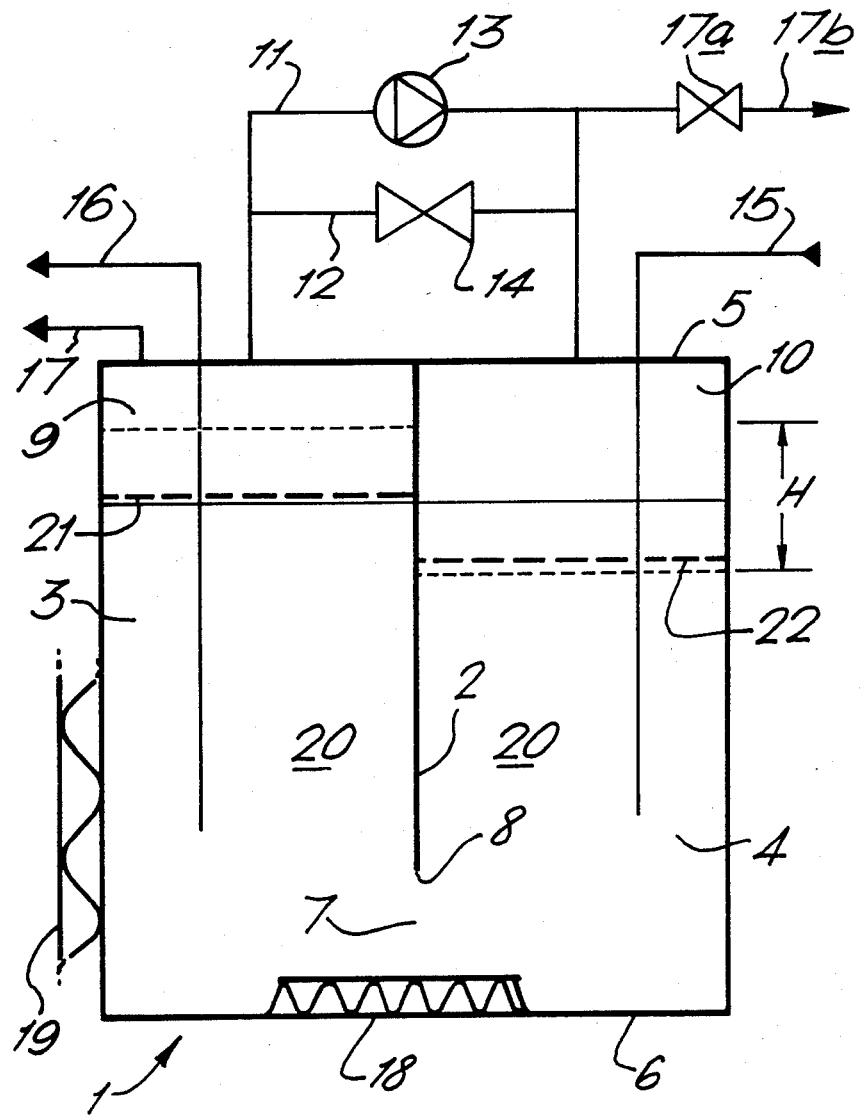

APPARATUS AND METHOD FOR THE TREATMENT OF ORGANIC WASTES

FIELD OF THE INVENTION

This invention relates to apparatus and a method for the treatment of organic wastewaters, sewage sludges, slurries and animal manures (hereinafter referred to collectively as organic waste), utilising an anaerobic microbial methane-producing process.

BACKGROUND OF THE INVENTION

Methods of treating organic wastes in anaerobic biological reactors, containing methanogenic and other anaerobic bacteria in suspended floc form are known. These methods involve the use of closed reaction vessels or digesters/reactors (hereinafter referred to as reactors) which are usually operated at a temperature of about 35° C. The suspended microbial biomass (reactor liquor) converts the biodegradable material in the influent wastes to biogas (a mixture of methane, carbon dioxide and minor amounts of other gases) and produces also a microbial cell residue (digested sludge). The biogas bubbles grow on the surfaces of liquor suspended solids, from which they are separated by the shearing action of a mixing system. The mixing system is generally related to the shape of the reactor. Reactors are generally of cylindrical construction with a domed roof and conical floor. Known methods of mixing include mechanical stirring by turbine or propellor, mixing by pumped recirculation of the liquor or gas mixing. The latter method involves recycling biogas from a gas pocket formed between the surface of the liquor and the reactor roof through one or more submerged outlets using a gas blower.

All of the known methods of mixing require mechanical equipment within the closed reactor. It is not feasible to inspect or carry out routine maintenance on such internally located equipment. For example, turbines and propellors may become fouled by fibrous materials; submerged gas manifold orifices may become clogged. The known systems also use significant amounts of energy in their operation.

SUMMARY OF THE INVENTION

It is an object of the present invention to provide an apparatus and method for the anaerobic digestion of organic wastes which eliminates the difficulties associated with conventional mixing systems, as outlined above, and which allow the designer flexiblity in selecting reactor shape.

According to a first aspect of the invention there is provided apparatus for the anaerobic conversion of organic waste as hereinbefore defined, to biogas using a microbial biomass, said apparatus comprising a closed reactor adapted to receive said organic waste the reactor comprising a first chamber and a second chamber in liquid communication, means for conveying biogas which accumulates in the second chamber to the first chamber with a corresponding displacement of liquid material from the first chamber to the second chamber, and means for rapidly equalizing gas pressure in the chambers with a concomitant rapid reverse displacement of said liquid material at predetermined intervals, resulting in an oscillating flow of liquid material in said reactor and an intimate mixing of the organic waste and the biomass, and means for releasing biogas from either of the chambers.

According to a second aspect of the invention there is provided a method for achieving an intimate and continuous mixing of organic waste as hereinbefore defined, with an anaerobic microbial biomass in a closed reactor, said method comprising feeding said organic waste to said reactor containing the microbial biomass, said reactor comprising a first chamber and a second chamber in liquid communication, allowing biogas to pass from the second chamber to the first chamber with a corresponding displacement of liquid material from the first chamber to the second chamber, rapidly equalizing the gas pressure in the chambers with a concomitant rapid reverse displacement of liquid material, resulting in an oscillating flow of liquid material in said reactor, and releasing gas from either the first chamber or the second chamber.

Preferably, the reactor comprises a single vessel partitioned internally thereof to define the first chamber and the second chamber.

Preferably, the reactor is divided into two equal-sized chambers by a substantially vertical wall which has a gas-tight junction with the top and sides of the reactor and terminates above the bottom of said reactor such that the two chambers are in liquid communication at their lower ends and whereby biogas accumulates in each chamber in a pocket between the top of the reactor and the liquid material in each chamber.

Preferably the means for conveying biogas from the second chamber to the first chamber comprises a gas blower housed in an external conduit which communicates with both chambers and allows a unidirectional transfer of biogas.

Preferably, the means for rapidly equalising the gas pressure in the two chambers comprises a quick-release valve housed in a further external conduit which communicates with both chambers.

The frequency of activation of the quick-release valve may be controlled by a timer switch or by a differential pressure switch responsive to a differential pressure between the gas pockets in said two chambers.

Preferably, a flow-restriction grid or baffle is provided in each of the chambers in staggered relationship relative to each other to promote release of biogas bubbles from the liquid material and thus prevent the formation of a floating solids layer at the liquid material/biogas interface.

The microbial biomass consists of methane-producing and other anaerobic bacteria and the biogas produced consists of a mixture of methane, carbon dioxide and minor amounts of other gases.

Organic waste is fed to the reactor through an inlet pipe or pipe manifold in the first chamber which discharges the organic waste below the surface of the liquor. Effluent is discharged from the reactor through an outlet system at the top of the second chamber which is so designed as to prevent the escape of biogas and promote the retention of microbial biomass.

Liquor is discharged through the outlet system in direct response to the inflow of organic waste into the reactor.

Preferably, the discharge of biogas occurs through a gas outlet pipe and passes through a water trap to a gas holder. The water trap will normally provide a fixed pressure in the range 75–500 mm.

The reactor is maintained at the preferred operating temperature of 35° C. by a heating system having an associated thermostatic control. The reactor is preferably insulated against heat loss.

The oscillating or "see-saw" flow of the liquor in the reactor, in addition to ensuring an intimate mixing of organic waste and biomass and prevention of particle segregation, also serves to reduce temperature gradients throughout the bulk liquor in the reactor.

The reactor may be a closed vessel of any desired shape with a gas-tight roof.

The required residence time of organic waste in the reactor depends on the type of waste being treated and the operating temperature. For example, for slurry-type wastes such as sewage sludge and animal manures, the preferred residence time at an operating temperature of 35° C. is in the range 10 to 20 days. For organic wastes such as dairy effluent which are more readily biograded, a shorter residence time is feasible.

The apparatus and method according to the invention have been found to be very efficient in converting organic wastes to biogas.

In laboratory tests using primary sewage sludge as the influent organic waste, 22 volumes of biogas per volume of sludge added were produced during a reactor residence time of 12 days and a reactor temperature of 35° C. The biogas produced contained in the region of 70% methane, the remainder of the biogas consisting mainly of carbon dioxide with minor amounts of other gases.

The mixing of organic waste and biomass using the apparatus and method according to the invention is far less expensive in terms of energy than conventional apparatus and methods.

In a preferred embodiment of apparatus according to the invention, energy is stored as the gas blower pumps gas from one gas pocket to the other in the respective compartments of the reactor and the energy is suddenly released when the quick-release valve is opened. The resulting rapid liquor flow prevents segregation of solids in the reactor and ensures a uniformity of consistency in the bulk liquor.

BRIEF DESCRIPTION OF THE DRAWING

The invention will be understood from the following description of an embodiment thereof given by way of example only with reference to the accompanying drawing which is a schematic representation of apparatus according to the invention.

DETAILED DESCRIPTION OF THE INENTION

Referring to the drawing there is illustrated a laboratory-scale apparatus comprising a reactor, indicated generally at 1, wherein organic waste is converted to biogas and which reactor 1 consists essentially of a rectangular tank partitioned internally thereof by a vertically disposed baffle wall 2 which divides said reactor 1 into two equal-sized compartments 3 and 4. The wall 2 has gas-tight junctions with the top 5 and a pair of opposed side walls of the reactor 1, respectively, and terminates above the bottom 6 of the reactor 1 such that the compartments 3 and 4 are in liquid communication via an aperture 7 defined by end 8 of the wall 2 and the bottom 6 of the reactor 1.

Biogas is trapped at the top of the reactor 1 in separate pockets 9, 10 in the compartments 3, 4, respectively. Compartments 3 and 4 communicate via a pair of externally located conduits 11 and 12 which house a gas blower 13 and a quick-release valve 14, respectively, for a purpose hereinafter described. An ancillary gas release valve 17a is also provided.

Organic waste is fed to the reactor 1 through an inlet pipe 15 and treated waste is discharged via an outlet pipe 16. Biogas produced in the reactor 1 is discharged via gas outlets 17 and 17b and passes through a water trap (not shown) to a gas holder (not shown).

The reactor contents may be heated to a constant temperature of 35° C. by hot water circulated through a heat exchanger 18. The reactor 1 is also thermally insulated as indicated at 19.

A horizontally disposed grid 21, 22 is provided in each of compartments 3, 4, respectively, adjacent the interface of reactor liquor 20 in each said compartment 3, 4 and their respective gas pockets 9, 10 for a purpose described below. The grids 21 and 22 are in staggered relationship.

In operation, continuous biogas evolution takes place in the reactor 1 due to the action of the microbial biomass on the organic waste in the bulk liquor 20. Biogas bubbles migrate upwards through the liquor 20 to the overlying gas pockets 9, 10.

Mixing of the reactor contents is achieved in the following way.

Starting with equal levels of liquor 20 in each compartment 3, 4 indicated by solid lines in the drawing, biogas is pumped from pocket 9 to pocket 10 via the conduit 11 by the gas blower 13 thereby causing a reverse flow of liquor 20 in the reactor 1 via the aperture 7. Accordingly, the level of liquor 20 rises in compartment 3 and falls in compartment 4 so that the level of liquor 20 in each compartment 3, 4 attains the level indicated by dotted lines in the drawing. When the differential head "H" reaches a preset value, typically in the range 100–500 mm the quick-release valve 14 is opened by a differential pressure switch (not shown) thereby creating a liquid jet from compartment 3 to compartment 4 via the aperture 7 and allowing a rapid equalization of gas pressure in compartments 3,4. The kinetic energy of the liquid jet is dissipated in turbulent mixing in compartment 4. Compartment 4 also receives a second mixing input in the form of the kinetic energy of the feed stream via the inlet pipe 15. The combination of these two inputs of kinetic energy to compartment 4 ensures an intimate mixing of the organic matter and the microbial biomass. The fermenting liquor in compartment 3 is subject to a much lower intensity of mixing than is that in compartment 4, being subject only to a vertical mass oscillation which is sufficient to detach biogas bubbles from particulate matter. This lower intensity or gentle mixing in compartment 3 promotes retention of the biomass in the reactor 1. This is particularly important where the reactor 1 is used to process liquid waste. The liquor 20 in the reactor 1 therefore undergoes an oscillating or "see-saw" motion viz liquor 20 in compartment 3 undergoes a slow rise followed by a rapid fall, while the liquor 20 in compartment 4 undergoes a slow fall followed by a rapid rise. During the continuous oscillating flow of the liquor 20 in the reactor 1, the liquor at and adjacent the surface in each compartment 3, 4 flows through the respective grid 21, 22 thereby promoting release of biogas attached to solid particles in said liquor 20. In particluar, the grids 21, 22 prevent the formation of a scum layer when the liquor 20 is a sewage sludge or a slurry. Furthermore, the kinetic energy of the liquid jet in passing from compartment 3 to compartment 4 prevents the build up of solids in the vicinity of the bottom 6 of the reactor 1 by sweeping the solids into compartment 4.

The gas blower 13 runs continuously, whereas the quick-release valve 14 is opened automatically by the differential pressure switch. In an alternative embodiment, a timer switch may be used to activate the quick-release valve rather than a differential pressure switch as used in the present embodiment.

The ancillary gas-release valve 17a is opened by a high liquid level detector (not shown) in the gas outlet 17 and is closed by a low liquid level detector also in the gas outlet 17. The release of gas through gas outlet 17b when valve 17a is opened prevents excessive discharge of liquid effluent through gas outlet 17.

It will be appreciated that the laboratory-scale apparatus depicted in the drawing and as described above can be readily scaled up to industrial scale.

The advantages of the apparatus and method according to the invention will be apparent from the above description. However, specifically, the advantages are as follows:

1. continuous mixing is provided at a very low level of energy input;
2. continuous mixing is provided without the use of any mechanical equipment within the reactor;
3. the mixing system allows the designer flexibility in selecting reactor shape;
4. the oscillating/see-saw flow reactor of the present invention is a highly efficient process reactor for the anaerobic biodegradation of organic matter. It has been shown to be capable of a high rate of biogas production per unit volume of reactor as hereinbefore described; and
5. The reactor has excellent biomass retention characteristics which obviate the necessity of recycling biomass from an external settling vessel when the reactor is used to treat liquid industrial wastes.

I claim:

1. Apparatus for the anaerobic conversion of organic waste such as organic waste waters, sewage sludge, slurries and animal manures to biogas using a microbial biomass, said apparatus comprising: a single vessel closed reactor for receiving said organic waste, said reactor comprising a first chamber and a second chamber in liquid communication with each other adjacent their lower ends; a generally vertical partition separating said first chamber and said second chamber, said generally vertical partition being in gas tight communication with the top of the vessel and having an aperture adjacent the bottom thereof; a gas blower for conveying biogas which accumulates in said second chamber to said first chamber with a corresponding displacement of liquid material from said first chamber to said second chamber; and means for rapidly equalizing gas pressure in said chambers with a concomitant rapid reverse displacement of said liquid material from said second chamber to said first chamber whereby a liquid jet is created by said aperture during said rapid reverse displacement of said liquid material thereby sweeping solids in the bottom of said closed reactor into said first chamber at predetermined intervals, resulting in an oscillating flow of liquid material in said reactor and in intimate mixing of said organic waste and said biomass, and means for releasing biogas from either of said chambers.

2. Apparatus as claimed in claim 1, in which said reactor is divided into two equal-sized chambers by a substantially vertical wall, said wall having a gas-tight junction with the top and sides of said reactor and terminating above the bottom of said reactor such that said two chambers are in liquid communication at their lower ends and whereby biogas accumulates in each chamber in a pocket between the top of said reactor and said liquid material in each chamber.

3. Apparatus as claimed in claim 2, in which said means for conveying biogas from said second chamber to said first chamber comprises a gas blower housed in an external conduit which conduit communicates with both chambers and allows a unidirectional transfer of biogas.

4. Apparatus as claimed in claim 3 in which said means for rapidly equalizing said gas pressure in said two chambers comprises a quick-release valve housed in a further external conduit which communicates with both chambers.

5. Apparatus as claimed in claim 4 in which the frequency of activation of said quick-release valve is controlled by a timer switch or by a differential pressure switch responsive to a differential pressure between said gas pockets in said two chambers.

6. Apparatus as claimed in claim 5 wherein a flow restriction grid or baffle is provided in each of said chambers in staggered relationship relative to each other to promote release of biogas bubbles from said liquid material and thus prevent the formation of a floating solids layer at the liquid material/biogas interface.

7. Apparatus as claimed in claim 6 wherein said organic waste is fed into said first chamber and biogas is released from said second chamber; the arrangement being such that, in use, when said quick release valve is closed, the level of the liquid material slowly falls in said first chamber to a level below said baffle therein and the level of the liquid material slowly rises in said second chamber to a level above said baffle therein; whereupon on the opening of said quick release valve, the level of the liquid material rises rapidly in said first chamber and up through said baffle therein and the level of the liquid material falls rapidly in said second chamber and down through said baffle therein; so that a turbulent mixing of said liquid material in said first chamber takes place by virtue of the passage of a jet of liquid material from said second chamber to said first chamber in the vicinity of the lower ends thereof.

8. A method for achieving an intimate and continuous mixing of organic waste such as organic waste waters, sewage sludge, slurries and animal manures with an anaeorbic microbial biomass in a closed reactor, said method comprising the steps of: feeding said organic waste to said reactor, as claimed in claim 1, containing the microbial biomass, said reactor comprising a first chamber and a second chamber in liquid communication, and allowing biogas to pass from said second chamber to said first chamber with a corresponding displacement of liquid material from said first chamber to said second chamber; rapidly equalizing the gas pressure in said chambers with a concomitant rapid reverse displacement of liquid material, resulting in an oscillating flow of liquid material in said reactor; and releasing biogas from either said first chamber or said second chamber.

9. Apparatus for anaerobic conversion of organic waste such as organic waste waters, sewage sludge, slurries and animal manures to biogas using a microbial biomass, comprising:

a single vessel closed reactor for receiving said organic waste partitioned internally thereof by a substantially vertical wall into a first chamber and a second chamber of substantially equal size, said wall being in gas-tight communication with the top of the vessel and terminating above the bottom of the vessel so that the two chambers are in liquid communication at their lower ends;

a gas blower housed in an external conduit which conduit communicates with both chambers and allows a unidirectional transfer of biogas which accumulates in said second chamber to said first chamber with a corresponding displacement of liquid material from said first chamber to said second chamber;

a quick release valve housed in a further external conduit which communicates with both chambers and allows for rapid equilization of gas pressure in said chambers with a concomitant rapid displacement of said liquid material at predetermined intervals resulting in an oscillating flow of liquid material in said vessel and intimate mixing of said organic waste and said biomass; and means for releasing biogas from either of said chambers.

10. Apparatus as claimed in claim 9, wherein a flow restriction grid or baffle is provided in each of said chambers in staggered relationship relative to each other to promote release of biogas bubbles from said liquid material and thus prevent the formation of a floating solids layer at the liquid material/biogas interface.

11. Apparatus as claimed in claim 10, wherein said organic waste is fed into said first chamber and biogas is released from said second chamber; the arrangement being such that, in use, when said quick release valve is closed, the level of the liquid material slowly falls in said first chamber to a level below said baffle therein and the level of the liquid material slowly rises in said second chamber to a level above said baffle therein; whereupon on the opening of said quick release valve, the level of liquid material rises rapidly in said first chamber and up through said baffle therein and the level of the liquid material falls rapidly in said second chamber and down through said baffle therein; so that a turbulent mixing of said liquid material in said first chamber takes place by virtue of the passage of a jet of liquid material from said second chamber to said first chamber in the vicinity of the lower ends thereof.

12. A method for achieving an intimate and continuous mixing of organic waste such as organic waste waters, sewage sludge, slurries and animal manures, with an anaerobic microbial biomass in a closed reactor, said method comprising: feeding said organic waste to said reactor containing the microbial biomass, said reactor comprising a single vessel partitioned internally thereof by a substantially vertical wall into a first chamber and a second chamber of substantially equal size, wherein said wall is in gas-tight communication with the top of the vessel and terminates above the bottom of the vessel so that the two chambers are in liquid communication at their lower ends; transferring biogas from said second chamber to said first chamber with a corresponding displacement of liquid material from said first chamber to said second chamber; rapidly equalizing the gas pressure in the chambers with a concomitant rapid reverse displacement of liquid material resulting in an oscillating flow of liquid material in said vessel; and releasing biogas from either the first chamber or the second chamber.

* * * * *